United States Patent [19]

De Baere

[11] Patent Number: 4,731,179
[45] Date of Patent: Mar. 15, 1988

[54] VESSEL FOR ANAEROBIC FERMENTATION

[75] Inventor: Luc De Baere, Gent, Belgium
[73] Assignee: Arbios S.A., Charleroi, Belgium
[21] Appl. No.: 846,095
[22] Filed: Mar. 31, 1986

[30] Foreign Application Priority Data

Apr. 2, 1985 [EP] European Pat. Off. .......... 85870050

[51] Int. Cl.⁴ .............................................. C02F 11/04
[52] U.S. Cl. .................................. 210/251; 210/319; 210/180
[58] Field of Search ............... 210/603, 180, 188, 224, 210/319, 532.1, 179, 251

[56] References Cited

U.S. PATENT DOCUMENTS

| | | | |
|---|---|---|---|
| 4,043,488 | 8/1977 | Halvorsen et al. | 222/233 |
| 4,198,211 | 4/1980 | Shattock | 210/603 X |
| 4,342,836 | 8/1982 | Harvey | 210/603 X |
| 4,451,372 | 5/1984 | Rovira | 210/603 |
| 4,514,297 | 4/1985 | Engvist | 210/603 X |
| 4,652,374 | 3/1987 | Cohen | 210/603 |

*Primary Examiner*—Tom Wyse
*Attorney, Agent, or Firm*—Schwartz, Jeffery, Schwaab, Mack, Blumenthal & Evans

[57] ABSTRACT

A flat plate vessel comprising an extraction device having a sliding frame on the flat plate, the frame being associated at least with one upwardly open channel, which is parallel to the flat plate and is provided with a transport screw, in which the vessel is first of all closed by a cover having an opening communicating with an inlet duct for material to be subjected to anaerobic fermentation and an opening communicating with a discharge duct for gas produced during fermentation; secondly, at least one activating shaft for the sliding frame and the drive shafts for the transport screws are surrounded by sealing gland devices; and finally, the channels provided with transport screws end at at least one discharge channel, the cross-section of which reduces towards the outlet opening, and in which there is located a transport screw extending towards the outlet opening, without however reaching this opening, and this screw forms, in the region of the discharge channel the cross-section of which narrows, a plug of fermented material of density sufficient to prevent escape of gas produced during anaerobic fermentation through the outlet opening of the discharge channel.

12 Claims, 3 Drawing Figures

VESSEL FOR ANAEROBIC FERMENTATION

BACKGROUND

1. Field of the Invention

The invention relates to vessels for anaerobic fermentation, and particularly to closed vessels with improved sealing means.

2. Related Art

It is already known to provide a device for extracting material in the form of a powder or in the form of particles, in a vessel or circular or polygonal cross-section having a bottom consisting of a flat plate. The known extraction device is in the form of a frame sliding on the flat plate and associated with several upwardly open channels, which are parallel to the flat plate of the vessel.

The known extraction device operates in the following manner: the frame sliding on the flat plate sweeps the material until it falls into the upwardly open channels. Then, the transport screws displace the material towards openings provided at the side, under the flat plate of the vessel.

SUMMARY

It is an object of the invention to modify such a known vessel so that it may be utilized as a reactor vessel for anaerobic fermentation.

According to the invention, the vessel is characterized first of all in that it is closed by a cover having at least one opening communicating with an inlet duct for material to be submitted to anaerobic fermentation and an opening communicating with a discharge duct for gas produced during fermentation, secondly in that the pistons or activating shafts for the sliding frame and the drive shafts for the transport screws are surrounded by sealing glands, and finally in that the channels equipped with transport screws terminate at at least one discharge channel, the cross-section of which narrows towards the outlet opening, and in which there is disposed a transport screw extending towards the outlet opening, without however reaching this opening, and the transport screw forms, in the region of the discharge channel the cross-section of which narrows, a plug of fermented material of a density sufficient to prevent escape of gas produced during anaerobic fermentation through the outlet opening of the discharge channel.

BRIEF DESCRIPTION OF THE DRAWINGS

The invention is explained hereinafter with reference to an example of an embodiment shown schematically in the attached drawing, wherein.

DETAILED DESCRIPTION OF THE INVENTION

Figure 1:
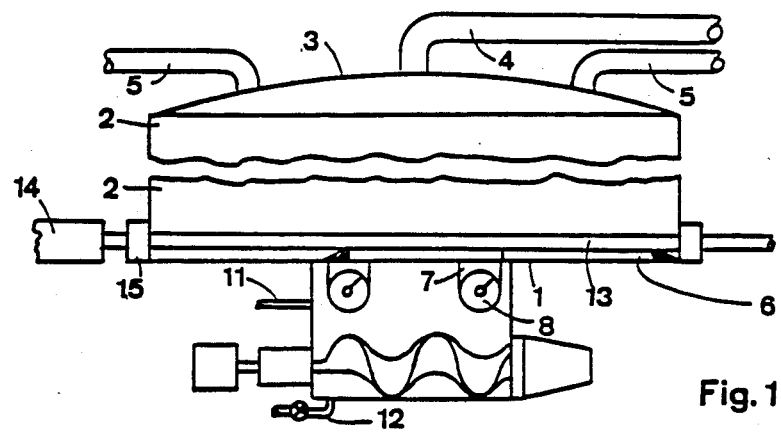
FIG. 1 of the drawing is a section of a vessel in elevation.
Figure 2:
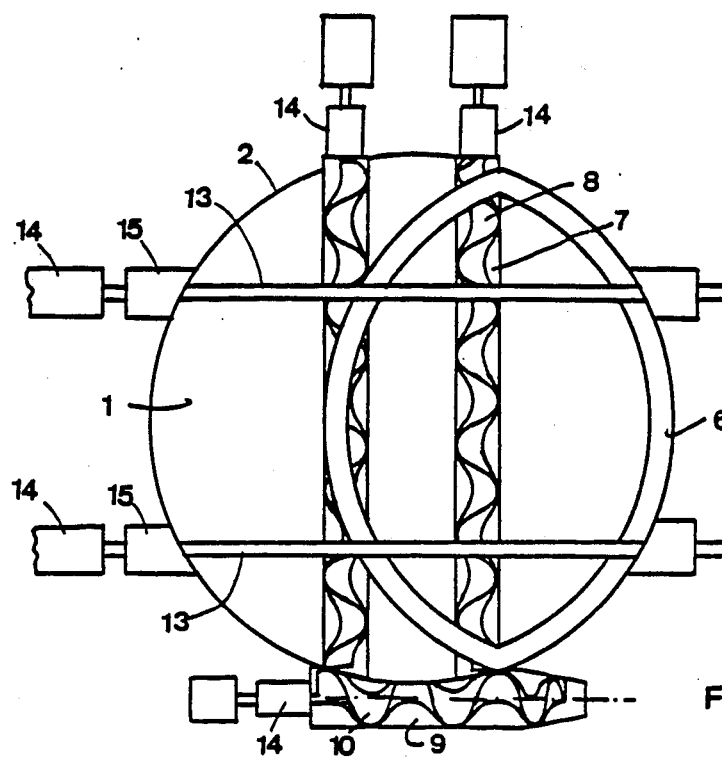
FIG. 2 is a section of a vessel in plan.

In FIGS. 1 and 2, a fermentation vessel is formed from a flat plate 1, a side wall 2 and a cover 3. In the cover, a central opening communicates with an outlet duct 4 for gas produced during fermentation, while other openings are connected to inlet ducts 5 for the material to be subjected to anaerobic fermentation. These inlet ducts are fed by one or more pumps, not shown, of the concrete-pump type. Due to its being transported by means of pumps, the material to be subjected to fermentation attains, in the inlet ducts 5, a density sufficient to prevent escape of gas produced through the inlet ducts 5. If several inlet ducts 5 terminate at different locations on the cover 3, it is possible to provide an arrangement, not illustrated, for advancing in turn the material in the different inlet ducts 5 and thus ensuring a good distribution of fresh material, and optinally recycled material, in the upper part of the reactor vessel. In order to withdraw the fermented material on the base of the vessel, a sliding frame 6 moves in a reciprocating manner on the base. In order to ensure a good standard of scraping, the frame 6 is formed from crossmembers in the form of a wedge, the members being disposed in such a way that the face of the wedge perpendicular to the base of the vessel defines a side directed towards extraction channels 7. These extraction channels are equipped with transport screws 8 and communicate with a discharge channel 9 located at the side of the vessel.

The cross-section of at least a part of the discharge channel 9 narrows to an increasing extent as it approaches the outlet opening of the channel 9. A transport screw 10 extending towards the outlet opening of the channel 9 is also disposed in the interior of the channel 9. The downstream end of the screw 10 is located in a part of the channel 9 where its cross-section narrows towards the outlet opening, but the screw does not reach to this outlet opening. In this way, a plug of fermented material is formed upstream of the outlet opening.

It is clearly possible to use a transport screw 10, the pitch of which varies along its axis, and in particular it is possible to use a screw, the pitch of which shortens at the downstream end, that is to say, at the location where the channel narrows, or where there is formed a plug of a density sufficient to avoid escape of fermentation gas through the outlet opening of channel 9. The space above the screw 10, on the upstream side, that is to say, on the side away from the outlet opening of channel 9, may be connected by means of a suitable connecting duct 11 to the gas outlet duct 4 leading from the cover. In addition, the discharge channel 9 is preferably inclined so that the material is entrained in it towards the top and the liquid squeezed out during the compression of the material forming the plug runs towards the bottom, or a purging device 12 may be provided, either acting intermittently or continuously. The outlet end of channel 9 may also be closed by a closure valve, not shown, during the periods when transport screw 10 is stationary.

The frame 6 is secured to one or more displaceable shafts 13 activated by one or more motor means, for example, hydraulic actuators 14.

At the locations where these displaceable shafts 13 pass through the vessel, sealing glands 15 are provided in order to prevent gas formed in the vessel from escaping along these shafts 13.

Glands of this kind are also provided at the locations where the drive shafts of screws 8 and 10 pass out.

Figure 3:
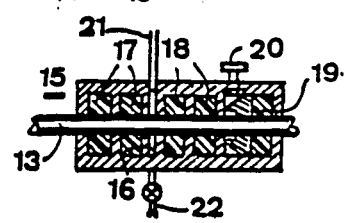
FIG. 3 represents a gland device.

At each location where one of the displaceable drive shafts 13 passes out of the vessel, a gland device 15 in accordance with FIG. 3 may be provided, this consisting of a chamber 16 between two glands 17 and 18. A supplementary gland 19 may also be provided, this being inactive during movement of the shafts 13 and provided with a locking device 20. A gland 19 of this kind is applied to shaft 13 by device 20 at the instant the shaft stops, to replace glands 17 and 18. The same arrangement of gland may be used at the locations where the drive shafts of transport screws 8 and 10 leave the boundary enclosing the reaction gas, that is to say the vessel and the channels 7 and 9. However, since the rotating glands around the drive shafts of screws 8 and 10 are subjected to only a relatively low degree of wear, it is possible to dispense with gland 19 and its locking device 20.

The chambers 16 of the various gland devices 15 are connected to the gas outlet duct 4 by means of a connecting duct 21. Similarly, the space in discharge channel 9 upstream of the plug located near the outlet opening is connected to the duct 4 by means of a duct 11. In this way, excessive local pressures causing escape of fermentation gas towards the exterior are avoided.

Like channel 9, each chamber 16 is also provided with purging means 22, either continuous or intermittent.

What is claimed is:

1. A flat plate vessel comprising:
an extraction device having a sliding frame on the flat plate, the frame cooperating with at least one upwardly open channel in and substantially parallel to the flat plate, said open channel being provided with a transport screw, a cover for closing the vessel having at least one opening communicting with an inlet duct for material to be subjected to anaerobic fermentation and an opening communicating with a discharge duct for gas produced during fermentation, at least one drive shaft for the sliding frame and a drive shaft for each transport screw, each said drive shaft being surrounded by a sealing gland device, each channel being equipped with a transport screw terminating at at least one discharge channel, the cross-section of which narrows said discharge channel narrowing towards the outlet opening and having a transport screw disposed therein and extending towards the outlet opening, without reaching the opening, whereby the transport screw forms, in the region of the discharge channel of narrow cross-section, a plug of fermented material of a density sufficient to prevent escape of gas produced during anaerobic fermentation through the outlet opening of the discharge channel.

2. A vessel according to claim 1, wherein the sealing gland devices include a chamber between two glands and wherein the chamber is connected to the discharge duct by means of a connecting duct.

3. A vessel according to claim 2, wherein the gland devices also include a gland located where a drive shaft passes out of the vessel and is provided with a locking device.

4. A vessel according to claim 3, wherein the space within the discharge channel upstream of the plug closing off its outlet opening is connected to the discharge duct by means of a connecting duct.

5. A vessel according to claim 3, wherein each chamber is provided with purging means.

6. A vessel according to claim 3, wherein the discharge channel includes a purging device.

7. A vessel according to claim 2, wherein each chamber is provided with purging means.

8. A vessel according to claim 2, wherein the space within the discharge channel upstream of the plug closing off its outlet opening is connected to the discharge duct by means of a connecting duct.

9. A vessel according to claim 2, wherein the discharge channel includes a purging device.

10. A vessel according to claim 1, wherein the space within the discharge channel upstream of the plug closing off its outlet opening is connected to the discharge duct by means of a connecting duct.

11. A vessel according to claim 10, wherein the discharge channel includes a purging device.

12. A vessel according to claim 1, wherein the discharge channel includes a purging device.

* * * * *